United States Patent [19]

Botich et al.

[11] Patent Number: 5,800,395
[45] Date of Patent: Sep. 1, 1998

[54] MEDICAL DEVICE WITH RETRACTABLE NEEDLE

[75] Inventors: Michael J. Botich, Oxnard; Thor R. Halseth, Simi Valley, both of Calif.

[73] Assignee: MDC Investment Holdings, Inc., Wilmington, Del.

[21] Appl. No.: 847,544

[22] Filed: Apr. 23, 1997

Related U.S. Application Data

[63] Continuation-in-part of Ser. No. 761,088, Dec. 5, 1996.

[51] Int. Cl.$^6$ .................................................. A61M 5/00
[52] U.S. Cl. .................................................. 604/110; 604/195
[58] Field of Search .................................... 604/110, 187, 604/192, 195, 198, 263

[56] References Cited

U.S. PATENT DOCUMENTS

| | | |
|---|---|---|
| 3,123,073 | 3/1964 | Barr, Sr. et al. . |
| 3,159,159 | 12/1964 | Cohen . |
| 3,306,290 | 2/1967 | Weltman . |
| 3,469,572 | 9/1969 | Nehring . |
| 3,874,367 | 4/1975 | Ayres . |
| 4,150,666 | 4/1979 | Brush . |
| 4,193,399 | 3/1980 | Robinson . |
| 4,307,731 | 12/1981 | Kaufman . |
| 4,418,703 | 12/1983 | Hoch et al. . |
| 4,507,117 | 3/1985 | Vining et al. . |
| 4,588,398 | 5/1986 | Daugherty . |
| 4,642,103 | 2/1987 | Gettig . |
| 4,661,300 | 4/1987 | Daugherty . |
| 4,664,657 | 5/1987 | Williamitis . |
| 4,710,170 | 12/1987 | Haber et al. . |
| 4,747,831 | 5/1988 | Kulli . |
| 4,758,231 | 7/1988 | Haber et al. . |
| 4,774,964 | 10/1988 | Bonaldo . |
| 4,790,827 | 12/1988 | Haber et al. . |
| 4,795,445 | 1/1989 | Jensen . |
| 4,813,426 | 3/1989 | Haber et al. . |
| 4,822,343 | 4/1989 | Beiser . |
| 4,838,863 | 6/1989 | Allard et al. . |
| 4,838,869 | 6/1989 | Allard . |
| 4,850,374 | 7/1989 | Diaz-Ramos . |
| 4,850,961 | 7/1989 | Wanderer . |
| 4,871,355 | 10/1989 | Kikkawa . |
| 4,892,107 | 1/1990 | Haber . |
| 4,900,307 | 2/1990 | Kulli . |
| 4,904,242 | 2/1990 | Kulli . |
| 4,915,702 | 4/1990 | Haber . |
| 4,917,101 | 4/1990 | Horn . |
| 4,927,414 | 5/1990 | Kulli . |
| 4,944,728 | 7/1990 | Carrell . |
| 4,947,863 | 8/1990 | Haber et al. . |
| 4,966,593 | 10/1990 | Lennox . |
| 4,973,316 | 11/1990 | Dysarz . |
| 4,978,343 | 12/1990 | Dysarz . |
| 4,994,034 | 2/1991 | Botich et al. . |
| 5,000,740 | 3/1991 | Duchaume . |
| 5,049,133 | 9/1991 | Pascual . |
| 5,053,010 | 10/1991 | McGary . |
| 5,064,419 | 11/1991 | Gaaude . |
| 5,067,490 | 11/1991 | Haber . |
| 5,070,885 | 12/1991 | Bonaldo . |
| 5,084,018 | 1/1992 | Tsao . |
| 5,086,780 | 2/1992 | Schmitt . |
| 5,092,853 | 3/1992 | Couvertier, II . |
| 5,102,394 | 4/1992 | Lasaitis . |
| 5,114,404 | 5/1992 | Paxton . |
| 5,114,410 | 5/1992 | Batle . |
| 5,125,414 | 6/1992 | Dysarz . |
| 5,129,884 | 7/1992 | Dysarz . |

(List continued on next page.)

*Primary Examiner*—John D. Yasko
*Attorney, Agent, or Firm*—Dann Dorfman Herrell & Skillman, P.C.

[57] ABSTRACT

A medical device having an automatically retractable needle is provided with a safety latch for preventing premature or inadvertent retraction of the needle. In a preferred embodiment, the medical device comprises an intravenous catheter or guide wire insertion device having a nose portion that is axially adjustable during assembly to provide a uniform needle length projecting from the forward end of the device.

17 Claims, 9 Drawing Sheets

U.S. PATENT DOCUMENTS

| | | |
|---|---|---|
| 5,135,505 | 8/1992 | Kaufman. |
| 5,167,641 | 12/1992 | Schmitz. |
| 5,176,650 | 1/1993 | Haining. |
| 5,180,369 | 1/1993 | Dysarz. |
| 5,180,370 | 1/1993 | Gillespie. |
| 5,185,006 | 2/1993 | Williamitis. |
| 5,188,599 | 2/1993 | Botich et al.. |
| 5,188,613 | 2/1993 | Shaw. |
| 5,201,710 | 4/1993 | Caselli. |
| 5,201,716 | 4/1993 | Richard. |
| 5,205,829 | 4/1993 | Lituchy. |
| 5,211,629 | 5/1993 | Pressly. |
| 5,215,525 | 6/1993 | Sturman. |
| 5,219,333 | 6/1993 | Sagstetter et al.. |
| 5,259,392 | 11/1993 | Schmitt. |
| 5,273,540 | 12/1993 | Luther. |
| 5,295,974 | 3/1994 | O'Laughlin. |
| 5,328,482 | 7/1994 | Sircom. |
| 5,376,075 | 12/1994 | Haughton. |
| 5,389,076 | 2/1995 | Shaw. |
| 5,395,337 | 3/1995 | Clemens. |
| 5,407,431 | 4/1995 | Botich et al.. |
| 5,407,436 | 4/1995 | Toft. |
| 5,423,758 | 6/1995 | Shaw. |
| 5,487,732 | 1/1996 | Jeffrey. |
| 5,487,734 | 1/1996 | Thorne. |
| 5,501,675 | 3/1996 | Erskine. |
| 5,518,004 | 5/1996 | Schraga. |
| 5,531,713 | 7/1996 | Mastronardi. |
| 5,545,146 | 8/1996 | Ishak. |
| 5,562,634 | 10/1996 | Flumene. |
| 5,573,510 | 11/1996 | Isaacson. |
| 5,575,777 | 11/1996 | Cover. |
| 5,584,809 | 12/1996 | Graba. |
| 5,611,781 | 3/1997 | Sircom et al.. |

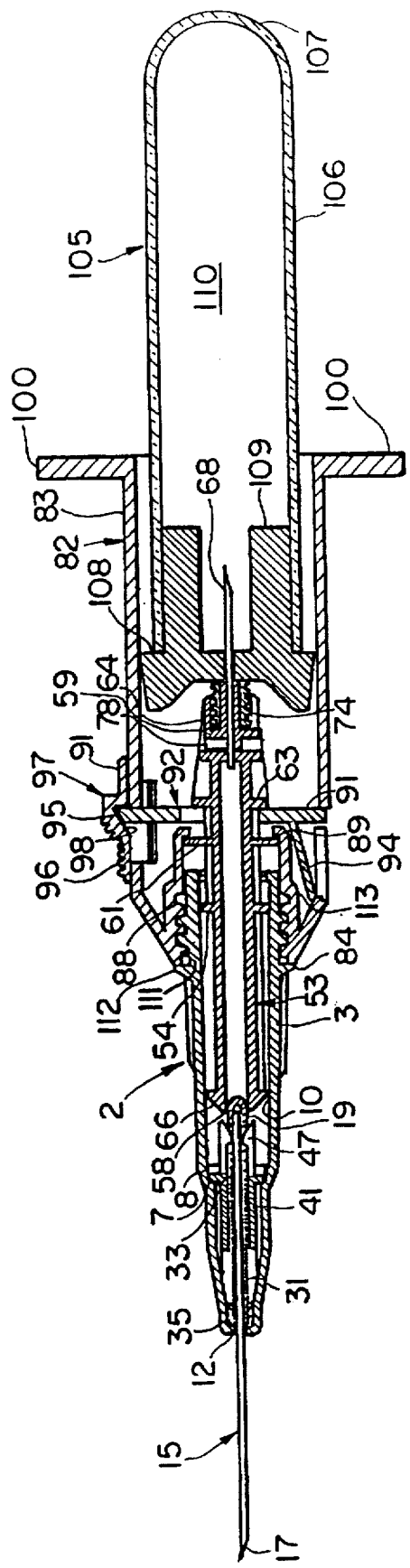
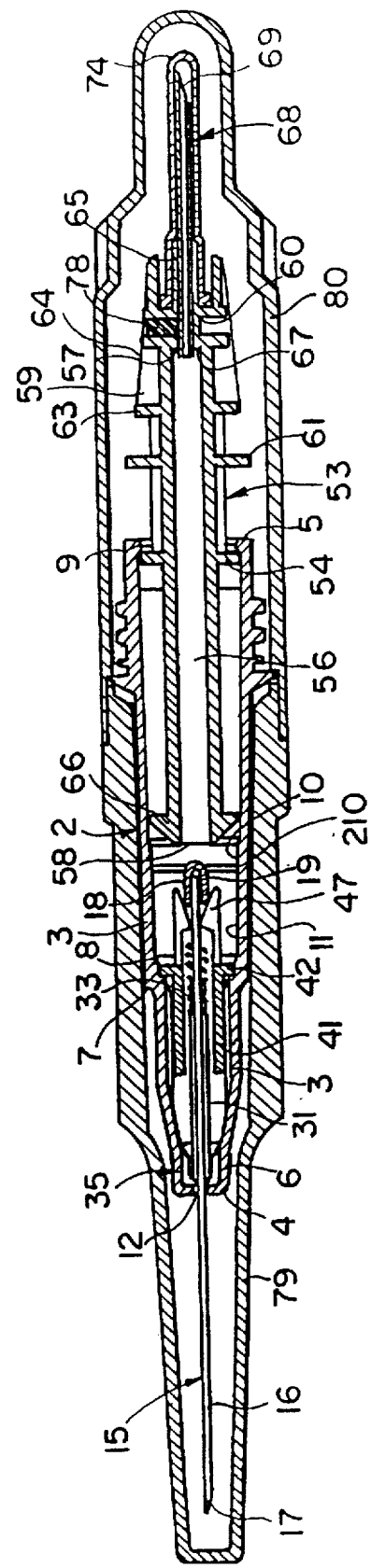
FIG. 1
FIG. 2

MEDICAL DEVICE WITH RETRACTABLE NEEDLE

This is a continuation-in-part of pending U.S. application Ser. No. 08/761,088, filed Dec. 5, 1996, pending which is incorporated by reference herein.

FIELD OF THE INVENTION

The present invention relates to needle-bearing medical devices used, for example, to insert catheters or guide wires into blood vessels of patients or to sample fluid from patients. More specifically, the invention relates to such a device having a retractable needle feature for rendering the device non-reusable and safely disposable.

BACKGROUND OF THE INVENTION

Various types of medical devices employ a needle for piercing the skin of a patient for diagnostic or therapeutic purposes. One such device is a blood collection device which includes a needle for piercing a blood vessel of the patient to allow blood to be sampled from the patient. When the needle is inserted into the blood vessel of the patient, blood is withdrawn through the needle into a vacuum collection tube. A second type of needle-bearing medical device is an intravenous catheter insertion device, wherein a needle-mounted catheter is positioned within a patient's vein. Once the catheter is properly positioned, the catheter insertion device is withdrawn leaving the catheter in place. Handling of such needle-bearing medical devices after the needle is withdrawn from the patient can result in transmission of various pathogens, most notably human immune virus (HIV), to uninfected medical personnel, due to an inadvertent needle prick.

Since the mid-1980s, concern over the risk of accidental needle stick injuries has spawned a number of design approaches for safety needle devices. Such devices can be broadly categorized as sliding sheath needle devices, wherein a physical barrier is positioned about the needle tip after use, and as needle-retraction devices, wherein the tip of the needle is retracted into the device after use. The category of needle retraction devices can be further subdivided into manual and automatic retraction devices. Manual retraction devices, as exemplified by U.S. Pat. Nos. 4,026,287 to Haller, 4,592,744 to Jagger, 4,808,169 to Haber et al. and 5,067,490 to Haber, require the user to pull or slide a needle-engaging mechanism rearwardly for a sufficient distance to retract the needle into the device. In automatic needle retraction devices, a biasing member, such as a spring, is employed to push or pull the needle into the device in response to activation of some release mechanism by the user. Such devices are exemplified by U.S. Pat. Nos. 4,813,426 to Haber et al. and 5,125,414 to Dysarz.

U.S. Pat. No. 4,747,831 assigned to Becton Dickinson and U.S. Pat. No. 4,900,307 to Kulli show respective automatic retractable-needle catheter stylets and syringes. The devices shown in the last-mentioned two patents are disclosed to be actuatable by the user who applies a simple unitary motion that entails a simple single-stage actuation movement in just one direction. Specifically, these latter patents show devices in which retraction is effected by depressing a single surface or member for a short distance in a single direction. Hence, during use of such devices, the user must be mindful not to prematurely trigger the needle retraction mechanism by accidentally contacting the surface for actuating the retraction mechanism. Since medical needle bearing devices are frequently employed under distracting circumstances, it would be desirable to provide an automatic needle retraction mechanism in which a compound action or dual motion is required by the user in order to effect automatic retraction of the needle. Such a mechanism would desirably require the user to act upon more than one surface of the retraction mechanism to effect withdrawal of the needle into the device. It further would be desirable to require that such actions to retract the needle occur along different directional axes to further decrease the likelihood of undesired premature or accidental retraction of the needle.

Of the aforementioned prior art devices which have automatic needle retraction mechanisms, all require a needle structure having an enlarged head, lip or rim extending radially outwardly from the axis of the needle to provide a block or enlarged surface on the needle which is biased toward retraction by the spring and which can be restrained against retraction by a latching arrangement or latch mechanism. In such devices, failure of the latch mechanism can occur to cause premature retraction of the needle. Hence, it would be desirable to provide an automatic needle retraction mechanism in which the latch mechanism operates more directly upon the needle.

After use of a needle bearing medical device, a small volume of contaminated fluid or blood may remain inside the needle after it is withdrawn from the patient. Depending upon the gauge of the needle used with the device, such residual fluid or blood may be ejected from the forward end of the needle during the rearward acceleration experienced in retraction of the needle. Such forward fluid ejection can result from insufficient capillary adhesion to retain the residual fluid against inertial forces during needle retraction, or against the hydraulic force exerted upon the residual fluid by inrushing fluid or air during rearward acceleration in retracting the needle. It would also be desirable to provide a structure in an automatic needle retraction device that would prevent such ejection of residual blood or fluid from the forward end of the needle during retraction.

SUMMARY OF THE INVENTION

In accordance with one aspect of the present invention, there is provided a needle retraction mechanism for a needle bearing medical device wherein a needle retaining member is bonded directly to the needle for selectively holding the needle in a projecting configuration from the device. The needle retaining member has an axial extension configured to provide at least one finger, and preferably a plurality of separable fingers that are joined about a central bore for holding the needle axially within the bore. Mutual engagement between the fingers and the needle can be enhanced by adhesive or thermal bonding. The needle retainer is positioned within the device to restrain the needle against rearward bias exerted upon the needle by a spring. The spring is preferably also bonded directly to the needle, so that neither the bias force or the counteracting restraining force is required to be mediated by any additional structure connected to the needle.

In accordance with another aspect of the present invention, the needle bearing medical device is provided with an automatic retraction mechanism in which the user is required to execute a dual or compound motion in order to actuate the needle for withdrawing the needle into the device by movement of a biasing member. The preferred compound motion requires the user to effect two motions on separate surfaces of the device. Furthermore, these motions are preferably designed to be effected in distinct directions in order to assure intentional needle retraction.

In accordance with another aspect of the present invention, a dual-motion needle retraction mechanism is provided in combination with respective catheter insertion and guide wire insertion devices.

BRIEF DESCRIPTION OF THE DRAWINGS

The foregoing summary, as well as the following detailed description of the preferred embodiments of the present invention, will be better understood when read in conjunction with the accompanying drawings, in which:

FIG. 1 is a sectional view of a retractable needle fluid collection device in accordance with the present invention;

FIG. 2 is an enlarged sectional view of the retractable needle assembly portion of the retractable needle fluid collection device of FIG. 1, showing the retractable needle assembly portion in an as-shipped configuration with front and rear protective caps positioned thereon;

DETAILED DESCRIPTION OF THE PREFERRED EMBODIMENTS

Figure 3:
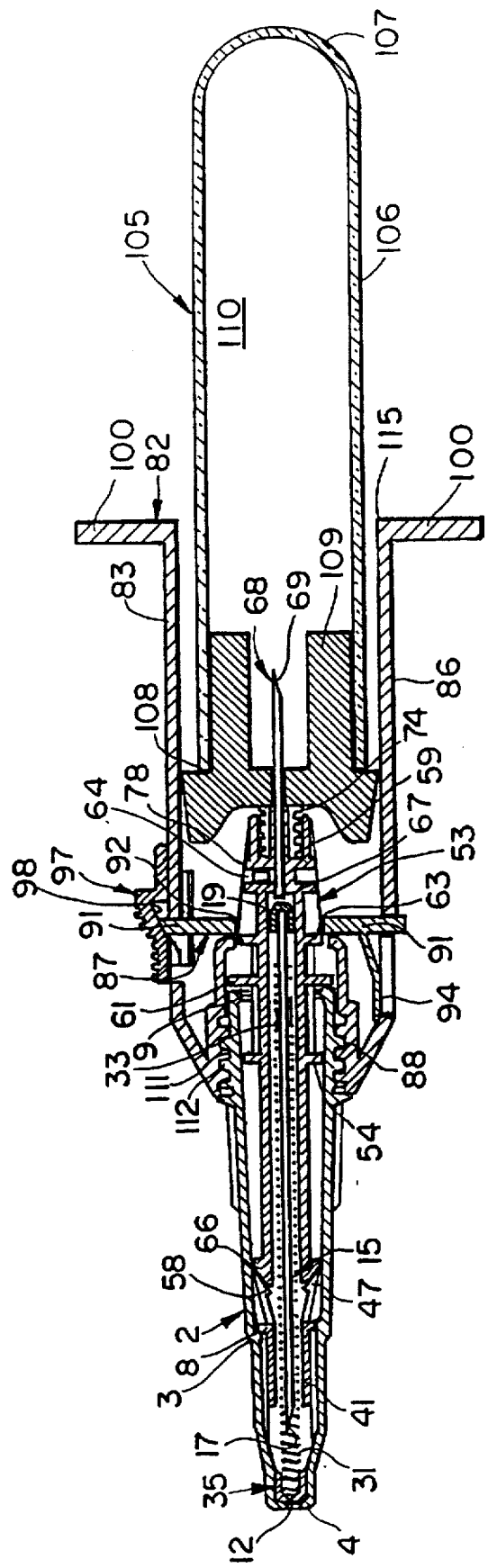
FIG. 3 is a sectional view of the retractable needle fluid collection device of FIG. 1, showing the needle in its retracted position.

Referring to FIG. 1, there is shown a fluid collection device in accordance with the present invention. The device comprises a needle carrier structure generally designated 2 for retaining a forwardly projecting needle 15 and a rearwardly projecting needle 68. A re-usable holder adapter generally designated 82 is mounted to the rear of the needle carrier structure for receiving a vacuum collection tube generally designated 105. After use of the device, the holder adapter 82 may be removed, and the needle carrier structure discarded.

The needle carrier structure 2 is shown in an as-shipped condition or configuration in FIG. 2. The needle carrier 2 comprises a barrel 3 having a partially closed forward end 4 and an open rear end 5. A needle 15 is positioned for use at the forward end 4 of the barrel 3 of the needle carrier 2. The needle 15 comprises a sharp forward end or tip 17 suitable for use in fluid sampling, such as for blood sampling by accessing a patient's vein. The needle 15 is preferably made of a biologically compatible material which can be easily sterilized, such as stainless steel. The forward portion of the needle 15 extends through an opening or axial hole 12 in the forward end 4 of the barrel 3 of the needle carrier 2. The rear portion of the needle 15 extends generally axially into the barrel 3 of the needle carrier 2. A second or rear needle 68 projects rearwardly from the needle carrier 2 into the areas of the holder adapter 82 which receives the vacuum collection tube 105.

During shipment, storage, or other handling of the needle carrier structure 2 prior to use, the tip 17 of the needle 15 is preferably surrounded and shielded by a front cap or sheath 79 that is removably attached to the exterior of the needle carrier 2. Likewise, the rear portion 73 of the rear needle 68 is preferably surrounded and shielded by a rear cap or sheath 80 during shipment, storage or other handling of the needle carrier structure 2 prior to use.

The front and rear caps 79 and 80, respectively, are held upon the needle carrier 2 by, for example, cooperative frictional engagement between the surface protrusion of the exterior of the needle carrier 2 and annular mating recesses of the front and rear caps 79 and 80, as shown in FIG. 2.

A spring 31 surrounds a portion of the needle 15 within the forward end of the barrel 3. The spring is compressed therein and connected to the needle 15 for biasing the needle 15 toward the rear end 5 of the barrel 3. The spring 31 is preferably bonded to the needle 15 by an adhesive 33, such as an epoxy, preferably an ultraviolet (UV) curable adhesive, such as "LOCTITE 3001", which is distributed by Loctite Corp. The spring 31 may be bonded to the needle 15 at a location spaced from the rear end of the spring 31, so that one or more coils of the spring 31 can be grasped during the bonding process to insure that the spring 31 and needle 15 are properly oriented and bonded together.

Figure 10:
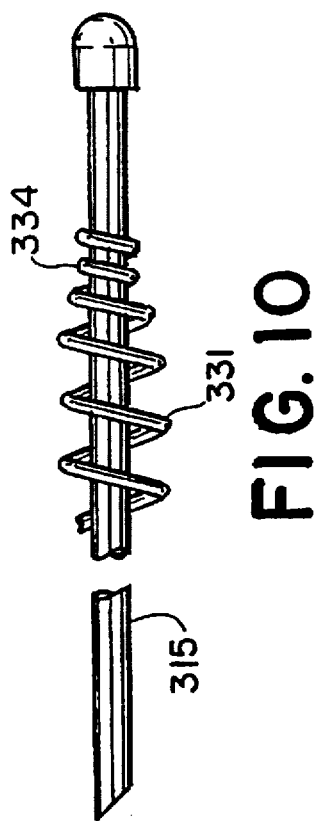
FIG. 10 is a side elevational view of an alternative arrangement for attaching the biasing spring to the retractable needle.

Alternatively, as shown in FIG. 10, wherein parts similar to those in FIG. 2 are shown by the same number designator with the addition of 300 thereto, the spring 331 may be attached to the needle 315 by crimping the spring 331 to the needle 315 to form a reduced diameter portion 334 for the spring 331. The spring 331 then exerts a rearward bias upon the needle 315 by virtue of a frictional engagement therebetween. In this arrangement, the reduced diameter portion 334 of the spring 331 may also be bonded to the needle 315 by adhesive to ensure permanent coupling of the spring to the needle.

Figure 9:
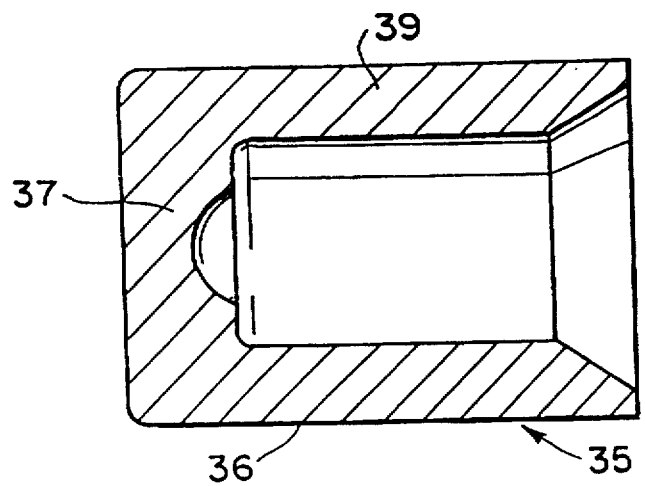
FIG. 9 is an enlarged sectional view of the sealing member for the end of the housing through which the retractable needle extends.

Referring again to FIG. 1, a sealing member 35, such as a resilient cup, washer, silicone plug puncturable disc or the like, is positioned within the forward end 4 of the barrel 3 of the needle carrier 2. As best seen in FIG. 9, the preferred sealing member 35 comprises a resilient cup 36. A puncturable membrane 37 forms the forward end 38 of the sealing member 35. The membrane 37 is sufficiently thin to be pierced by the tip 17 of the needle 15 to allow the needle 15 to extend outwardly from the forward end 4 of the barrel 3 of the needle carrier 2. In this extended configuration for the needle from the needle carrier, the membrane 37 provides a fluid-tight seal about the interior of the axial hole 12 in the forward end 4 of the barrel 3. The membrane 37 is sufficiently resilient to seal the axial hole 12 after the needle 15 has been retracted, to prevent fluid from leaking out of the barrel 3 when the needle is retracted. The sealing member 35 also promotes axial alignment of the needle 15 and the spring 31 within the barrel 3, by holding the forward end 40 of the spring 31 within a tubular portion 39 of the resilient cup 36. Additionally, the sealing member 35 helps to protect the tip 17 of the needle 15 from being damaged by contact with the interior of the barrel 3 when the needle 15 is inserted into the barrel 3 during assembly.

Referring again to FIG. 2, a needle retainer 41 is positioned within a forward portion of the barrel 3 for selectively retaining the needle 15 in a configuration projecting outwardly from the needle carrier. A flange 42 is formed on the needle retainer 41 for engagement with a complementary groove 7 formed about the interior of the barrel 3 for orienting and fixing the needle retainer in position. An annular detent 8 is formed on the inner surface of the barrel 3 of the needle carrier 2 to prevent the needle retainer 41 from being dislodged from its position in the needle carrier 2. Holding of the needle retainer 41 in position in the interior of the barrel 3 may be further assured by epoxy or ultrasonic welding.

The forward end 43 of the needle retainer 41 is generally cylindrical. An axial bore 44 is formed in the needle retainer 41 for housing a portion of the needle 15 and the spring 31. The rear portion of the needle retainer 41 is provided with a latching structure or mechanism for selectively retaining the needle 15 in its projecting position from the needle carrier 2.

Figure 6:
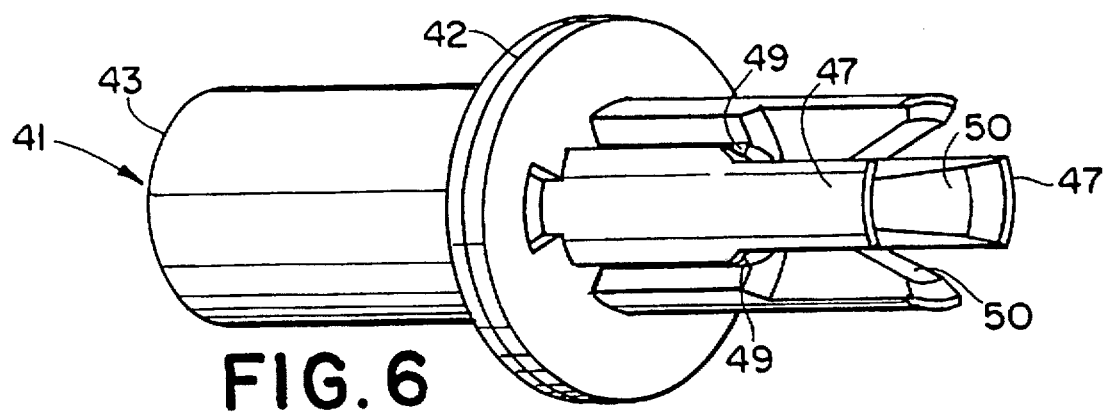
FIG. 6 is a side elevational view of a needle retainer structure for selectively holding the needle of a retractable needle medical device.
Figure 7:
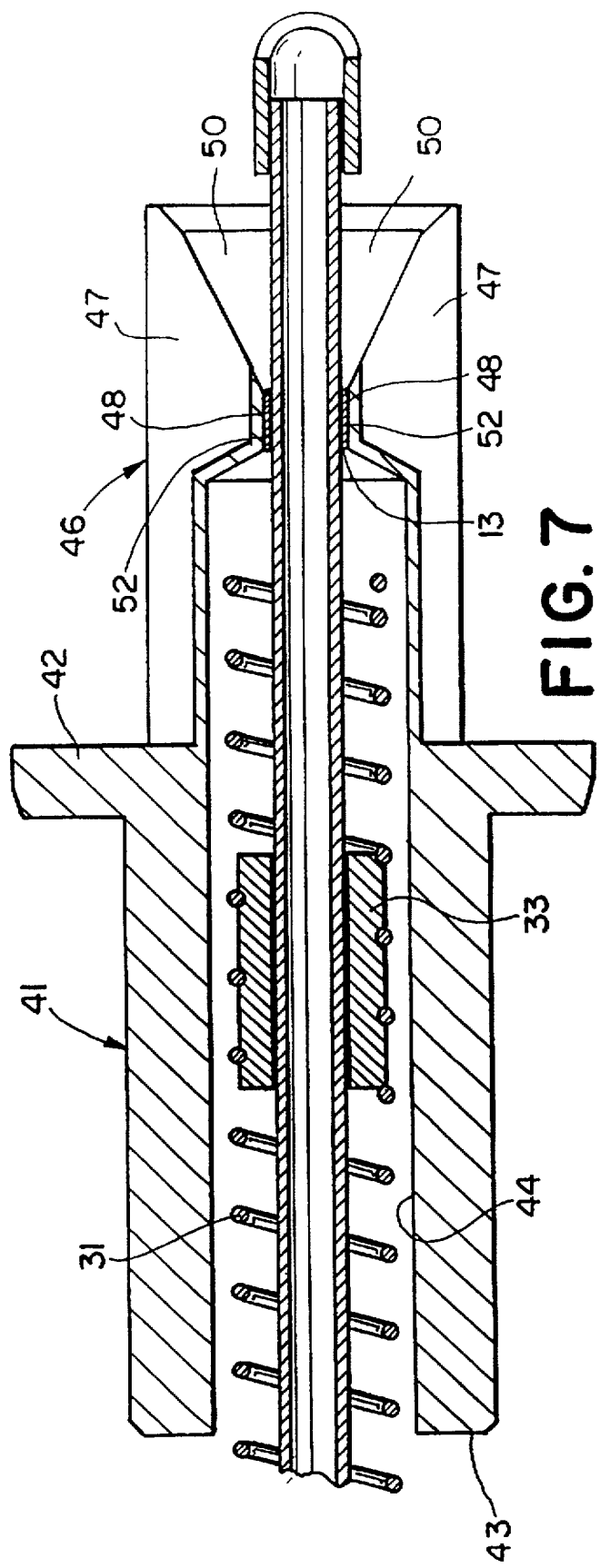
FIG. 7 is an enlarged sectional view of the needle retainer with an associated needle and biasing spring.

The engagement between the needle 15 and the needle retainer 41 is best seen in the enlarged view in FIG. 7. The latching structure or mechanism is preferably divided into a plurality of latching projections or fingers 47, which are formed at the rear end of the needle retainer 41, as shown in FIG. 6. When the needle retainer is positioned in the needle carrier, the fingers 47 extend axially rearward into the interior of the barrel 3 of the needle carrier 2. The fingers 47 are formed to have radially inwardly directed protrusions having interior surfaces 48 in FIG. 7, forming a constricted portion 13 in bore 44 of the needle retainer. The surfaces 48 are substantially parallel to the axial surface of the needle 15. The surfaces 48 are configured to conform to the outer surface of the needle 15 to thereby maintain the needle 15 in axial alignment within the needle retainer 41. The surfaces 48 of the fingers 47 preferably form a continuous surface within the interior of the needle retainer 41 to enhance engagement with the needle 15. The continuous axial surface between the fingers 47 also provides a seal with the needle 15, so that fluid is kept out of the axial bore 44 in the needle retainer 41 during use in collecting fluid.

The surfaces 48 of the fingers 47 are secured or bonded to the outer surface of the needle 15 using an adhesive 52, such as one of the adhesives or epoxies listed in Table 1 below. The preferred adhesive 52 for a particular application will depend on such variables as the strength of the spring 31, the surface area of the constricted portion 13 of the bore 44, and the material of which the fingers 47 and the needle are manufactured.

TABLE 1

| Adhesive Type | Supplier Designation | Supplier |
| --- | --- | --- |
| Epoxy | EP30 | MasterBond |
| Epoxy | EP21LV | MasterBond |
| Epoxy | 301 RTC | Epoxy Technology |
| Epoxy | 353 RTC | Epoxy Technology |

TABLE 1-continued

| Adhesive Type | Supplier Designation | Supplier |
| --- | --- | --- |
| Epoxy | E32 | Permabond |
| Epoxy | C-7/A-34 | Armstrong |
| Epoxy | 3501 B/A Grey | Scotch-Weld |
| Epoxy | 3501 B/A Clear | Scotch-Weld |
| Epoxy | Henkel Versamid 125 catalyst/Shell Epon 828 resin | Henkel/Shell |
| Epoxy | Eccobond 1962-31 | W.R. Grace |
| Epoxy | Eccobond 927-10E | W.R. Grace |
| Epoxy | FDA-2 | Tracon |
| Epoxy | Eccobond LA 2843-23 | W.R. Grace |
| Cyanoacrylate | 4011 | Loctite |
| Cyanoacrylate | 4013 | Loctite |
| Cyanoacrylate | 4161 | Loctite |
| UV cured adhesive | 3001 | Loctite |
| UV cured adhesive | 3011 | Loctite |
| UV cured adhesive | UV 9006 | W.R. Grace |
| UV cured adhesive | UV 9007 | W.R. Grace |
| UV cured adhesive | UV 9008 | W.R. Grace |

As can be seen most clearly in FIG. 6, the needle retainer preferable comprises four fingers 47, but one or more fingers 47 may be employed depending on such factors as the size of the device and the nature of the biasing member (i.e., spring 31), for effecting optimum operation in holding the needle and facilitating needle retraction.

The exterior of needle retainer 41 is provided with longitudinal grooves or score lines 49 between the fingers 47 to facilitate separation of the fingers and breakage of the fingers 47 when the retraction of the needle is actuated.

In the initial configuration of the needle carrier shown in FIG. 1, the needle retainer 41 is positioned in the forward portion of the barrel. The spring 31 surrounds the needle 15 and is compressed between the rear of the sealing member 35 at the forward end 4 of the barrel 3 and the location at which the spring 31 is bonded to the needle 15 by adhesive 33. Hence, the needle 15 is biased toward the rear end 5 of the barrel 3 of the needle carrier 2 and is held by the needle retainer fingers 47 against the bias of the spring.

Figure 8:
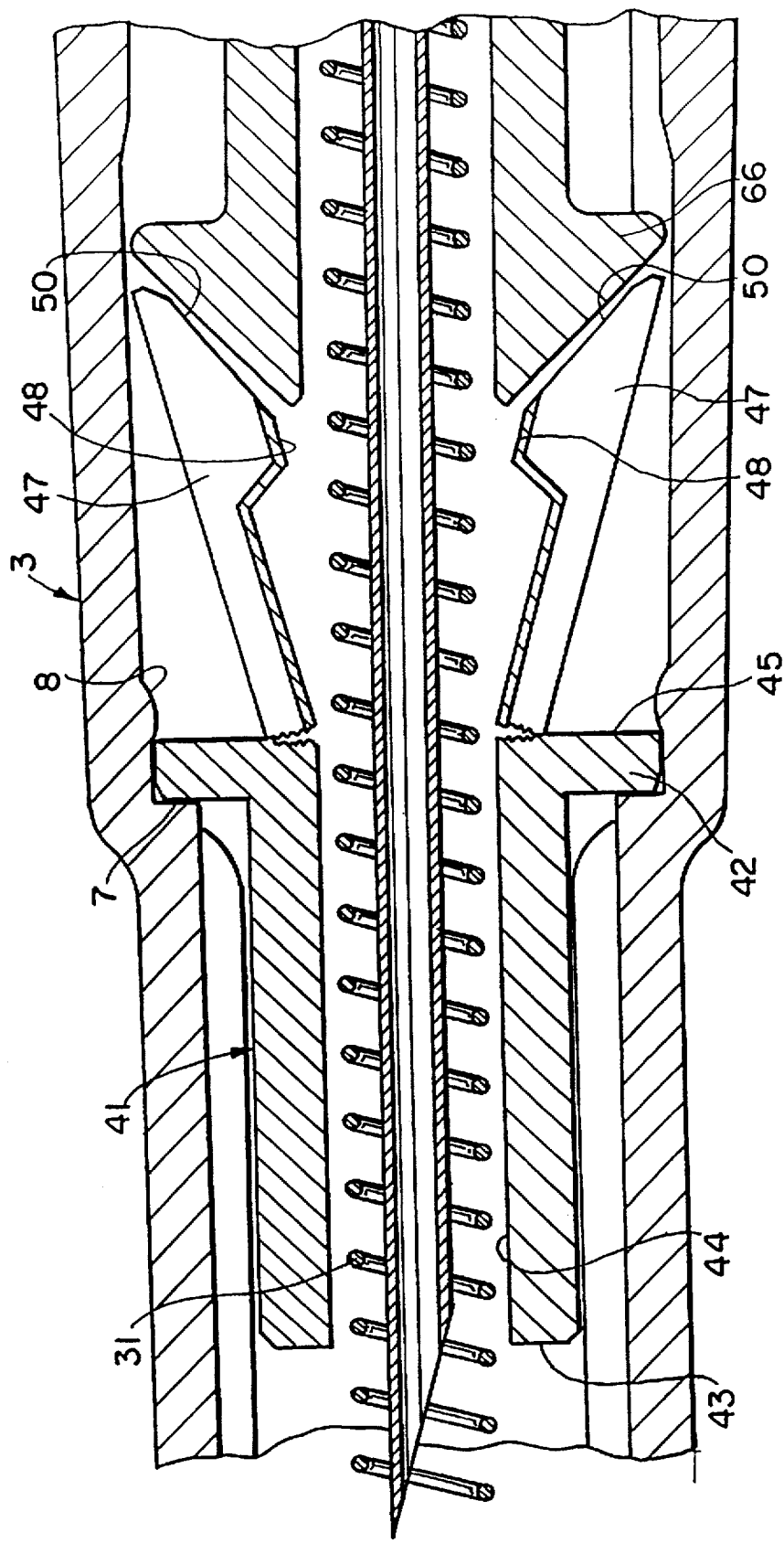
FIG. 8 is an enlarged fragmentary sectional view of the needle retainer, showing the condition of the needle retainer, needle and biasing spring after retraction.

Referring again to FIG. 7, the fingers 47 are preferably flexible to permit outward movement to break the bond between the needle 15 and the retainer surfaces 48 in order to release the fingers 47 from the needle 15. Additionally, the fingers could be fractured when moved outwardly to release the needle. The fingers 47 are formed to have canted or wedge-shaped rearwardly facing surfaces 50 to facilitate engagement and spreading of the fingers 47, as described more fully herein below. As shown in FIG. 8, when the fingers 47 are deformed or flexed radially outwardly to release the fingers 47 from the needle 15, the expansive force of the spring 31 immediately thrusts the needle 15 toward the rear end 5 of the barrel 3 of the needle carrier 2. Thus, the sharp end of the needle 15 is drawn into the barrel 3 to prevent accidental touching of the needle after use.

Referring again to FIG. 2, an actuating member generally designated 53 is slidably positioned in the rear end 5 of the barrel 3 of the needle carrier 2. The actuating member 53 is manufactured from a material which is chemically compatible with the fluid being collected. For example, the actuating member 53 may be made from polystyrene, which is suitable for use with blood collection devices. Alternatively, chemical compatibility may be provided by a conformal coating or layer of a chemically inert material, such as polytetrafluoroethylene, upon the surfaces of the actuating member 53 that come into contact with the fluid being collected.

The actuating member 53 is generally cylindrical and is adapted to be received within the rear end of the barrel 3. The actuating member 53 has a flange 54 formed thereon for engagement with the interior of the barrel 3 to position and guide the actuating member during movement. A detent 9 is formed on the inner surface of the barrel 3 so that the flange 54 can be forced by the detent 9 during assembly, and thereafter prevented from being withdrawn from the barrel 3.

The actuating member 53 includes structural features for effecting release of the needle 15 from the needle retainer 41. The forward end of the actuating member 53 comprises a tapered head 66 formed thereon, which provides a frustro-conical forward surface. The forward surface of the head 66 provides an annular shoulder that is complementarily contoured or tapered to mate with the outwardly flared rearward surfaces 50 of the fingers 47 of the needle retainer 41. To release the bond between the surfaces 48 of the fingers 47 and the needle 15, the actuating member 53 is urged forward within the barrel 3 to spread the fingers outward by cooperative engagement between the head 66 and the rear surfaces 50 of the fingers, as shown in FIG. 8.

In the as-shipped configuration shown in FIG. 2, the actuating member 53 is initially located at its initial or rearward position in the barrel 3, such that the flange 54 abuts with the detent 9 at the rear of the barrel 3. The head 66 of the actuating member 53, in addition to providing a release mechanism for the needle 15, is sized to provide a fluid seal between the interior of the barrel 3 and the periphery of the head 66. During shipment or storage of the needle carrier, the material of which the actuating member 53 and the head 66 are formed may creep or deform to compromise the integrity of the fluid seal provided by the head 66. In order to ensure a fluid tight seal prior to use of the device, the barrel 3 includes a reduced-diameter portion 10 located along the interior surface of the barrel 3 in the forward direction relative to the first position of the head 66. Immediately prior to use of the needle carrier, the actuating member 53 is advanced within the body to a second or intermediate, position as shown in FIG. 1. In the second position of the actuating member 53, the head 66 is positioned within the reduced diameter portion 10 of the barrel 3. The constrictive force exerted on the head 66 by the interior of the barrel 3 insures the integrity of the fluid seal provided therebetween. Advancement of the actuating member 53 to the second position is automatically effected when the holder adapter 82 is connected to the needle carrier, as described hereinbelow.

Referring again to FIG. 2, the actuating member 53 has a hollow interior defining a chamber 56 having an open forward end 58 and a partially-closed or reduced diameter open rear end 57. The chamber 56 is sized to allow the needle 15 along with the attached spring 31 to be received into the chamber 56. The rear end 57 of the chamber 56 has an axial bore 60 formed therein which has a smaller diameter than the chamber 56. Accordingly, a rear wall 67 is formed where the axial bore 60 adjoins the chamber 56. When the actuating member 53 is actuated for retraction of the needle 15, the spring 31 propels the needle rearwardly 15. The needle 15 and spring 31 are thereby propelled toward the rear of the chamber 56, and the rear wall 67 acts as a stop for the spring 31 and the needle 15.

An elastomeric boot 74 is positioned over the rear portion of the rear needle 68. During insertion of the device into the patient's vein, the boot 74 prevents fluid from prematurely flowing out from the needle carrier 2, and provides a visual indicator, when it receives fluid, that the needle 15 is properly inserted within the vein of the patient. When the needle 15 is properly inserted into the patient, fluid flows through the needle 15 and fills a "flashback" chamber defined by the interior of the barrel 3 of the needle carrier 2, the chamber 56 of the actuating member 53, the rear needle 68, and the interior of the boot 74. To facilitate such operation, gas is vented from the flashback chamber by hairline vents or grooves (not shown) formed between the boot and the actuating member.

Referring again to FIG. 1, the holder adapter 82 comprises a housing 83 which is configured to be removably engaged to the barrel 3 of the needle carrier 2. The forward end 84 of the housing 83 comprises an axial bore 88 having internal threads 111 for engagement with corresponding external threads 112 found on the rear end of the barrel 3 of the needle carrier 2.

A concentric tubular forward portion 113 extends rearwardly to form the forward end of the tube adapter 82. The tubular portion has an inwardly-directed lip 89 formed thereon. The lip 89 is positioned to abut with a radial flange 61 on the actuating member 53 to drive the actuating member 61 into the second or intermediate position within the barrel 3 of the needle carrier 2, when the holder adapter 82 is fixed or connected to the needle carrier. As the tube adapter 82 is screwed onto the needle carrier 2, the forward surface of the lip 89 pushes on the rear surface of the radial flange 61, thereby forcing the actuating member 53 to move forward within the barrel 3 of the needle carrier 2 until the head 66 of the actuating member 53 is positioned in the reduced diameter portion 10 of the barrel 3.

The holder adapter 82 includes a gate or safety actuator mechanism generally designated 87 to prevent accidental or premature retraction of the needle 15. The gate mechanism preferably comprises a slide member 91 extends across the interior of the housing 83 of holder adapter 82. An eccentric bore 92 is formed through the slide member 91. The slide member 91 is transversely slidable within the housing 83 from a locked position to an unlocked position. The eccentric bore 92 is formed in the slide member 91 to facilitate the slide member acting as a step for flange 63 of the actuating member. Hence, the bore 92 is ordinarily displaced from the longitudinal axis of the actuating member 53 so that the rear surface of slide member 91 abuts with a flange 63 of the actuating member 53 in a locked position to prevent forward motion of the actuating member 53, avoiding inadvertent premature retraction of the needle 15.

The slide member 91 further includes a biasing portion 94 for biasing the slide member 91 to the locked position. The biasing portion 94 is sufficiently flexible to yield when a transverse force is applied to displace the slide member 91 towards an unlocked position. In the unlocked position, the bore 92 is aligned with the flange 63, so that the actuating member 53 can be further moved toward the front of the barrel. The biasing portion 94 is sufficiently resilient to return to its original shape when the transverse force is released. The biasing portion 94 is provided by a portion of the slide member which is formed to provide a biasing member.

To facilitate connection of the holder adapter 82 to the needle carrier 2, the rear end 59 of the actuating member 53 may have a conical camming surface 64 for aligning the slide member 91 with the longitudinal axis of the actuating member during installation of the holder adapter 82 onto the needle carrier 2. Hence, as the holder adapter 82 is mated to the rear of the needle carrier, the camming surface 64 urges the rim of the eccentric bore 92 into alignment with the actuating member 53. Then, when the tube adapter reaches the position shown in FIG. 2, the biasing portion 94 urges the slide member 91 into overlapping abutment with flange 63.

A slide button or actuator 97 is provided on the exterior of the housing 83 to facilitate activation of the slide member 91 prior to retracting the needle 15. In the configuration shown in FIG. 3, the slide button 97 can be pushed rearwardly by the user to cause the slide member 91 to be moved transversely from the locked position to the unlocked position. The button 97 has a slanted or beveled inner surface 98 formed thereon to abut with a slanted outer surface 95 of the slide member 91 in order to cam against the outer surface 95 when the button is pushed. The outer surface of the button 97 may include ridges or serrations 96 to provide traction with the user's finger. In an alternative embodiment (not shown), the button can be designed to be depressed in order to move the slide member from the locked position to the unlocked position.

External projections, providing finger grips 100, are formed along the exterior of the housing 83 of the holder adapter 82 to allow the user to more easily maneuver and manipulate the device. In a preferred embodiment, the finger grips 100 are positioned so that the user can grip the device between two fingers while exerting forward pressure against the rear of the collection tube 105 to maneuver a collection tube into position and cause retraction of the needle, as explained below.

The rear end of the holder adapter 82 is sized to receive a collection tube 105 for receiving the fluid to be collected. The collection tube 105 comprises a generally cylindrical body 106 having a closed rear end 107 and an open forward end 108. The forward end 108 of the collection tube 105 is sealed by a puncturable plug member 109. In this arrangement, an interior chamber 110 is defined within the collection tube 105. The plug 109 seals the forward end 108 of the collection tube 105 so that a vacuum or reduced pressure can be maintained within the chamber 110. The collection tube 105 can be removably inserted into the holder adapter 82 by inserting the forward end 108 of the collection tube 105 into the housing 83 of the holder adapter 82. As the collection tube 105 is inserted, the rear needle 68 punctures the plug 109.

As previously mentioned, when the needle 15 is released from the needle retainer 41, the needle is thrust rearwardly to be received in the chamber 56 of the actuating member 53. Because the needle 15 may contain a volume of residual fluid therein, it is desirable to prevent such fluid from being ejected from the forward end of the needle as the needle is accelerated rearwardly by the spring during needle retraction. Accordingly, there is provided means for preventing such ejection of fluid from the needle of blood collection device of the present invention. One such means is a check valve 19, which may be mounted to the rear end of the needle 15 for preventing fluid from being expelled through the forward end of the needle 15 as the needle 15 is being retracted.

Figure 5:
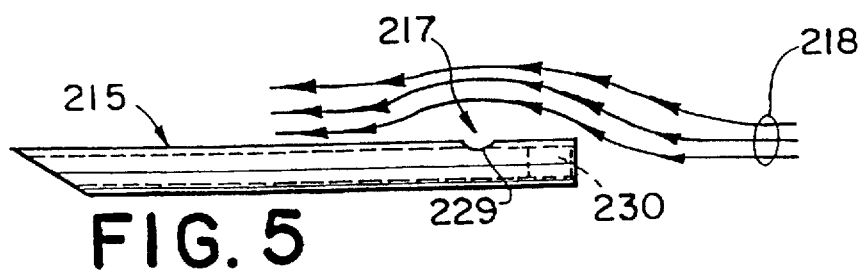
FIG. 5 is a perspective view of a needle for use in retractable needle medical devices and illustrating lines of fluid flow about the needle during retraction.

One embodiment of a means to prevent ejection of fluid from the needle during retraction is shown in FIG. 5. A hole 229 is formed in the side of the needle 215 and a plug 230 is positioned in the rear end 218 of the needle. When the needle 215 is propelled rearwardly during retraction of the needle 215, gas or fluid in the chamber, into which the needle is moving, is forced to flow over the closed rear end of the needle 215, as indicated by lines 216. The hole 229 is positioned sufficiently toward the rear of the needle such that it is located adjacent a region 217 of reduced air pressure created by the stream lines 216 of fluid or gas around the closed rear end of the needle. For needles having sizes ranging from 25 gauge to 20 gauge, holes of about 0.020 to about 0.080 inches in diameter located at about 0.030 to about 0.10 inches from the rear end of the needle are within a range effective to substantially prevent fluid from being ejected from the forward end of the needle as it is accelerated rearwardly into retraction. In a preferred embodiment of a 21 gauge needle, a hole of about 0.05 inches in diameter centered at about 0.07 inches from the rear end of the needle has been shown to be effective. In other embodiments, such parameters as the length and mass of the needle, and the force constant of the spring, will affect the selection of appropriate dimensional parameters for determining the arrangement for preventing forward fluid ejection.

Figure 4:
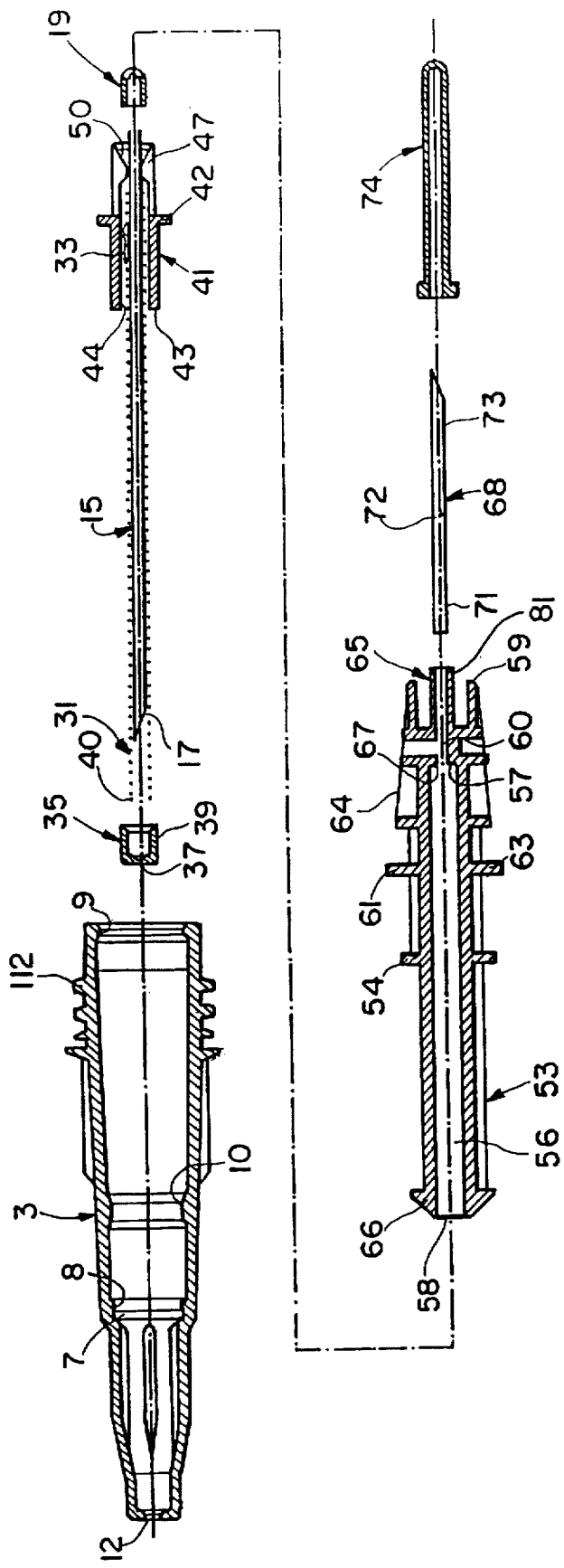
FIG. 4 is an exploded sectional view of the needle carrier assembly of the device of FIG. 1.

The needle carrier 2 can be assembled as shown with reference to the exploded view of FIG. 4. The spring 31 is bonded to the needle 15 with adhesive 33. The needle 15 is then axially positioned within the needle retainer 41. The surfaces 48 of the needle retainer 41 are then secured to the needle 15. Valve 19 is positioned onto the rear end of the needle 15. The sealing member 35 is positioned in the forward portion of the barrel 3 of the needle carrier 2. Alternatively, the sealing member 35 can be positioned onto the forward end 40 of the spring 31. The needle retainer 41, needle 15, and spring 31 are then inserted into the rear end 5 of the barrel 3 of the needle carrier 2 until the needle retainer 41 seats within groove 7 on the interior of the barrel 3 of the needle carrier 2.

The forward portion 71 of the rear needle 68 is then secured in the axial bore 60 of the actuating member 53. The boot 74 is positioned over the rear needle 68 and secured to the rear end of the actuating member 53. The forward end 55 of the actuating member 53 is then inserted into the rear end of the needle carrier 2. The actuating member 53 is advanced to the initial or first position within the barrel 3, so that the first radial flange 54 of the actuating member 53 passes over the second detent 9 along the inner surface of the barrel 3 of the needle carrier 2. If the device is not to be used at this time, front and rear caps, 79 and 80, are then positioned over the needle 15 and the rear needle 68, as shown in FIG. 2.

Prior to use of the device, the front and/or rear caps, 79 and 80, are removed from the needle carrier 2. The holder adapter 82 is mounted on the needle carrier 2 by engaging the internal threads 111 on the holder adapter 82 with the external threads 112 of the needle carrier 2 in a screw-type motion to assume the configuration shown in FIG. 1. The screwing motion causes the lip 89 on the tubular portion 113 of the tube adapter 82 to advance the actuating member 53 to the second position, such that the forward end of the actuating member 53 is in close proximity to the rear portion 45 of the needle retainer 41. In the second position, the radial flange 63 of the actuating member 53 abuts against the slide member 91 of the safety actuator or gate mechanism 87.

The needle 15 can then be inserted into a patient (i.e., into a blood vessel of the patient for blood sampling). The user then verifies that the needle 15 is properly inserted in the patient's blood vessel by looking for the appearance of fluid in the flashback chamber area in the needle carrier 2. When the needle 15 has been properly inserted into the patient, the collection tube 105 is inserted by the user into the rear end of the tube adapter 82. As the collection tube 105 is advanced therein, the rear needle 68 pierces the boot 74 and the plug 109, and the boot 74 is compressed by the plug 109 down the shaft of the rear needle. When the rear end of the rear needle 68 enters the chamber 110 of the collection tube 105, fluid is drawn into the chamber 110 of the collection tube 105 by the vacuum or reduced pressure within the collection tube 105.

When the collection tube 105 is filled, or a desired amount of fluid has been collected, the collection tube 105 can be withdrawn from the holder adapter 82. Subsequent collection tubes can be filled in substantially the same manner. When the last desired collection tube has been filled, the needle 15 is withdrawn from the patient's blood vessel while maintaining the collection tube in the holder adapter 82.

The needle 15 can now be retracted by the user. To initiate retraction, the device can be gripped between two of the user's fingers while the rear end 107 of the collection tube 105 is positioned against the palm of the user's hand. For example, if the barrel is held between the thumb and the middle finger, the rear of the collection tube 105 may be placed against the palm, while the index finger is extended along the barrel to actuate the button 97 of the safety gate mechanism. The button 97 is then moved rearwardly, thereby laterally displacing the slide member 91 within the barrel to bring the eccentric bore 92 of the slide member 91 into axial alignment with the flange 63 of the actuating member 53. While maintaining the slide member 91 in the unlocked position, the collection tube 105 is further advanced in a forward direction relative to the barrel by applying pressure to the rear end 107 of the collection tube 105 with the palm of the user's hand. Movement of the collection tube 105 in the forward direction urges the forward end of the actuating member 53 against the fingers 47 on the needle retainer 41. The fingers 47 are thereupon spread radially outwardly by the force of the forward end of the actuating member 53. When the fingers 47 are spread radially outwardly, the surfaces 48 of the fingers 47 are disengaged from the needle 15, that is the bond between the fingers and needle is broken. Accordingly, the needle 15 is then propelled rearwardly, by expansion of the biasing spring 31, into the chamber 56 of the actuating member 53. The needle 15 in its retracted position in the device is shown in FIG. 3. The collection tube 105 can then be removed and the needle carrier 2 and holder adapter 82 can safely be discarded. Alternatively, the holder adapter may be removed from the needle carrier for subsequent re-use.

Figure 11:
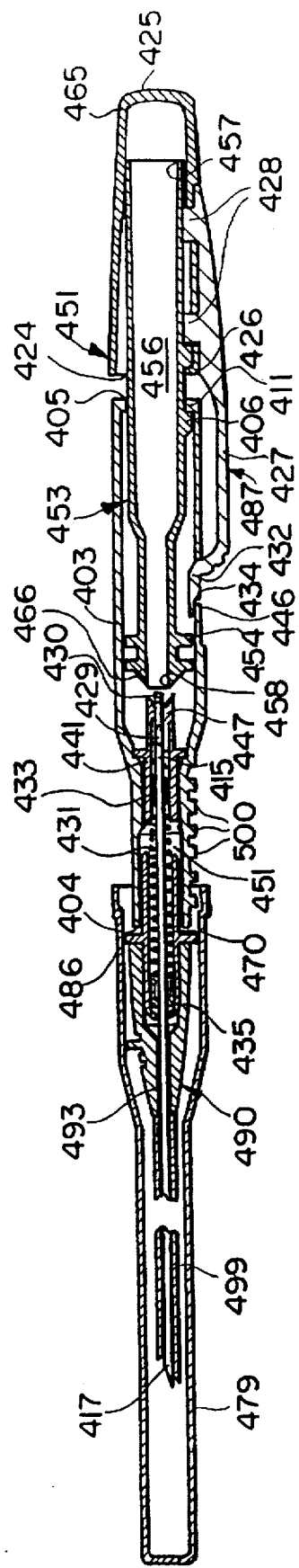
FIG. 11 is a sectional view of a catheter insertion device in accordance with the present invention shown in an as-shipped configuration with a catheter and a front protective cap positioned thereon.

Referring to FIG. 11, there is shown a catheter insertion device in accordance with the present invention. The device comprises a barrel 403 and an actuating assembly generally designated 451 inserted within the rear end 405 of the barrel 403. A needle retainer 441 and nose piece 470 are provided to releasably maintain a needle 415 in a projecting configuration from the barrel 403. It should be noted that those elements of the catheter insertion device which are analogous to similar elements of the embodiment of the blood collection needle of FIG. 1 are designated by adding 400 to the reference numerals used for those elements with respect to the blood collection needle.

The barrel 403 has an open forward end 404 and an open rear end 405. The needle 415 is positioned for use at the forward end 404 of the barrel 403. The needle 415 comprises a sharp forward end or tip 417 suitable for use in catheter insertion. The needle 415 is preferably made of a biologically compatible material which can be easily sterilized, such as stainless steel. The forward portion of the needle 415 extends through the open forward end 404 of the barrel 403 and protrudes from the front end of the nose piece 470. The rear portion of the needle 415 extends generally axially into the barrel 403. External grooves or ridges, providing finger grips 500, are formed along the exterior surface of the barrel 403 to enable the user to easily grasp the device without slippage.

During shipment, storage, or other handling of the device prior to use, the tip 417 of the needle 415 is preferably surrounded and shielded by a front cap or sheath 479 that is removably attached to the exterior of the barrel 403. The front cap 479 is held upon the barrel 403 by, for example, cooperative frictional engagement between a radial flange 486 on the nose piece 470 and the interior surface of the front cap 479, as shown in FIG. 11.

A needle retainer 441 is positioned within a forward portion of the barrel 403 for selectively retaining the needle 415 in a configuration projecting outwardly from the forward end of the barrel 403. The needle retainer 441 is substantially identical to the needle retainer 41 described above in reference to the embodiment of the present invention describing the fluid collection device.

Figure 12:
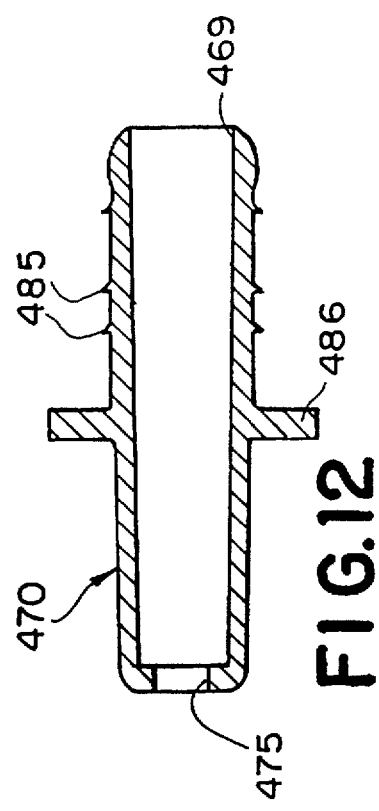
FIG. 12 is an enlarged sectional view of the nose piece of the catheter insertion device of FIG. 11.

A nose piece 470 is positioned within the forward end of the barrel 403. As shown in FIG. 12, the nose piece 470 comprises a generally cylindrical member having an open rear end 469 and a partially open forward end 475. The nose piece 470 is positioned within the barrel 403 by inserting the rear end 469 of the nose piece 470 through the open front end 404 of the barrel 403. Accordingly, the outer diameter of the nose piece 470 is sized to fit snugly within the inner diameter of the front end 404 of the barrel 403 so that, when assembled, a fluid tight seal is formed between the nose piece 470 and the barrel 403. Toward that end, an annular projection 485 may be formed along the exterior surface of the nose piece 470 to assist in providing an enhanced fluid tight seal.

Figure 13:
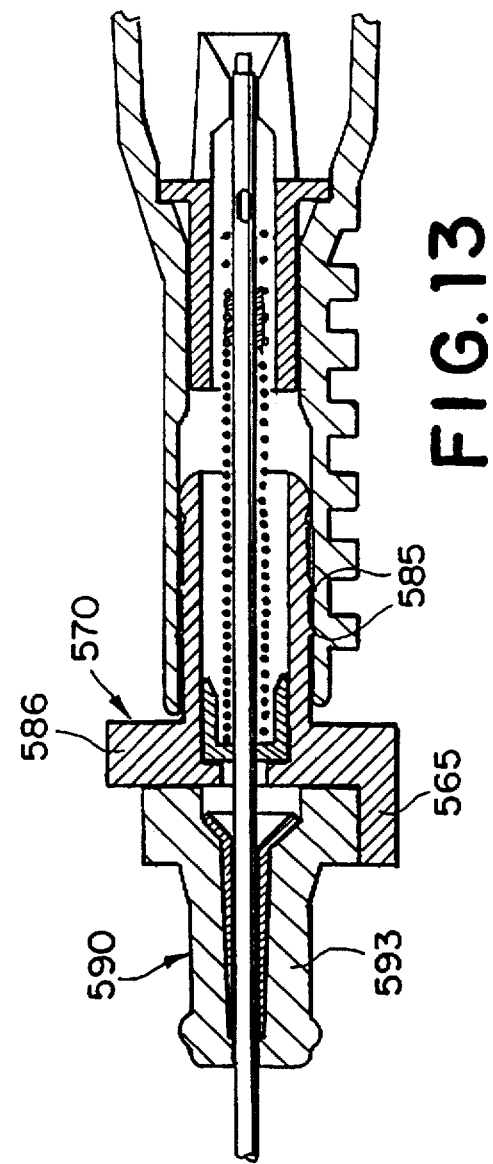
FIG. 13 is a fragmentary sectional view of a second embodiment of the central portion of a catheter insertion device in accordance with the present invention.

In an alternate arrangement, depicted in FIG. 13, the nose piece 570 includes a catheter stabilizing means for preventing rotation of the catheter 590 while the catheter 590 is being positioned within a patient. The catheter stabilizing means comprises a projection 565 which extends from the radial flange 586. The projection 565 abuts against a surface of the catheter hub 593, thereby restricting the catheter 590 from rotating.

A spring 431 surrounds a portion of the needle 415 within the forward end of the barrel 403. The spring 431 is compressed within the nose piece 470 and attached to the needle 415 for biasing the needle 415 toward the rear end 405 of the barrel 403. The spring 431 is preferably connected to the needle 415 in the ways described above in reference to FIGS. 7 and 10.

Referring again to FIG. 11, a sealing member 435, such as a resilient cup, washer, silicone plug puncturable disc or the like, is positioned within the forward end of the nose piece 470. The preferred sealing member 435 comprises a resilient cup 436 as discussed above in reference to FIG. 9.

Because the needle 415 may contain a volume of residual blood therein after insertion of the catheter, it is desirable to provide a means for preventing ejection of blood from the needle 415 as the needle 415 is retracted. One such means, which is particularly suitable, includes a hole 429 in the side of the needle 415 and a plug 430 blocking the rear end of the needle 415. Hole 429 and plug 430 are similar to the arrangement of hole 29 and plug 30, described above in reference to FIG. 5.

When the needle 415 is properly inserted into the patient, blood flows through the hole 429 in the needle 415 and fills a "flashback" chamber 451 defined by the interior of the nose piece 470, the interior of a forward section of the barrel 403, and the interior of the needle retainer 441. To facilitate such operation, the needle 417 is bonded to the bore of the needle retainer 441 so that the side hole 429 in the needle is positioned at a forward axial location in the barrel relative to the point of attachment between the needle and the needle retainer. Hence, blood entering through the needle will be confined to the flashback chamber. As blood enters the chamber, displaced gas is vented from the flashback chamber 451 through hairline vents or grooves (not shown) formed in the exterior surface of the nose piece 470 or on the interior surface of the forward section of the barrel 403. The vents are desirably sized to allow the surface tension and viscosity of the blood to prevent blood from leaking through the vents. Similar vents are provided between the rear cap and the actuating member to vent displaced gas from the device.

In the configuration in FIG. 11, the needle retainer 441 is positioned in the forward portion of the barrel 403. The spring 431 surrounds the needle 415 and is compressed between the sealing member 435 at the forward end of the nose piece 470 and the location at which the spring 431 is bonded to the needle 415 by adhesive 433. Hence, the needle 415 is biased toward the rear end 405 of the barrel 403 and is held by the needle retainer fingers 447 against the bias of the spring 415.

The actuating member, generally designated 453, is slidably positioned in the rear end 405 of the barrel 403. The actuating member 453 is manufactured from a material which is chemically compatible with blood, such as polystyrene. The actuating member 453 has a flange 454 formed thereon for engagement with the interior of the barrel 403 to position and guide the actuating member 453 during movement. The actuating member 453 also includes a raised projection 406. An annular lip 411 is formed on the inner surface of the rear end 405 of barrel 403 so that the raised projection 406 can be forced into the barrel during assembly, and thereafter the actuating member 453 is retained by the lip 411 and prevented from being withdrawn from the barrel 403.

The actuating member 453 further includes structural features for effecting release of the needle 415 from the needle retainer 441. The forward end of the actuating member 453 comprises a tapered head 466 formed thereon. The tapered head 466 of actuating member 453 functions in an analogous manner to the tapered head 66 of the actuating member 53 described in reference to FIG. 1.

The actuating member 453 has a hollow interior defining a chamber 456 having an open forward end 458. The rear end 457 of the chamber 456 can be either open, as shown, or closed. The chamber 456 is sized to allow the needle 415 along with the attached spring 431 to be received into the chamber 456. When the actuating member 453 is actuated for retraction of the needle 415, releasing the needle retainer from the needle, the spring 431 propels the needle 415 rearwardly. The needle 415 and spring 431 are thereby propelled toward the rear of the chamber 456. A rear cap 465, as described below, provides a stop for the spring 431 and the needle 415. Alternatively, if the rear end of the actuating member 453 is closed, the interior surface at the end 457 of the actuating member 453 provides a stop.

The rear cap 465 is positioned over a rear portion of the actuating member 453 as shown in FIG. 11. The rear cap 465 comprises a generally tubular structure having an open forward end 424 and a closed rear end 425. The open forward end 424 of the rear cap 465 is positioned over the rear end 457 of the actuating member 453. To insure that the rear cap 465 fits snugly over the actuating member 453, the inner diameter of the rear cap 465 preferably tapers from the forward end 424 towards the rear end 425. To prevent removal of the rear cap 465, the forward end 424 of the rear cap 465 is provided with an annular lip 426 which frictionally engages the exterior surface of the actuating member 453.

A locking mechanism 487 is provided for preventing inadvertent or premature retraction of the needle 415. In the preferred embodiment, the locking mechanism comprises a resilient arm 427 attached to the rear cap 465. As shown in FIG. 11, the resilient lever arm 427 is attached to the rear cap 465 by two tabs 428, which are shaped and positioned to mate in a snap fit with two slots 429 located along the rear cap 465. Alternatively, the lever arm 427 may be integrally formed with the rear cap 465. When attached to the rear cap 465, the lever arm 427 forms a cantilever along the exterior surface of the barrel 403.

A catching member 432 is provided at the forward end of the lever arm 427. In the embodiment shown in FIG. 11, the catching member 432 comprises a stop shoulder 434 to limit movement of the rear cap 465 toward the front or needle end of the device, and, hence, the actuating member 453 is prevented from being actuated, in a forward direction. In operation, when the rear cap 465 and actuating member 453 are assembled to the barrel 403, the catching member 432 is positioned, against the bias of the resilient lever arm 427, within a cut-out section of the barrel 403. The stop shoulder 434 abuts a rearward-facing surface 446 of the barrel 403, thereby restricting forward motion of the rear cap 465. When in this position, the actuating member 453 is prevented from being moved to effect retraction of the needle 415. However, the locking mechanism 487 can be activated to permit needle retraction as described below.

The device can be assembled as shown with reference to the view of FIG. 11. The rear end of the needle 415 is closed by a plug 430. The spring 431 is bonded to the needle 415 with adhesive 433. The needle 415 is then positioned into the bore of the needle retainer 441. The holding surfaces of the needle retainer 441 are then secured to the needle 415, preferably by bonding. The sealing member 435 is positioned in the forward portion of the nose piece 470. Alternatively, the sealing member 435 can be positioned onto the forward end 440 of the spring 431. The needle retainer 441, needle 415, and spring 431 are then inserted into the rear end 405 of the barrel 403 until the needle retainer 441 seats within groove 407 on the interior of the barrel 403. The nose piece 470 is then attached to the front end of the barrel 403.

The axial position of the nose piece 470 can be adjusted within the barrel 403, prior to securing the nose piece to the barrel, in order to compensate for manufacturing variations in the lengths of needles available for assembly. The catheter 490 functions optimally when the forward end of the catheter tube 499 is positioned precisely at the rear end of the tapered tip 417 of the needle 415. After the needle retainer 441, with the needle 415 secured therein, is positioned within the barrel 403, adhesive may be applied to the interior forward surface of the barrel 403. Then, the nose piece 470 is placed into the rear of the catheter hub 493. The nose piece 470 is urged into the forward end of the barrel 403 by pressing the catheter hub 493 rearward while sliding the catheter tube 499 onto the needle 415. As the nose piece 470 is urged into the barrel 403, the spring 431 is compressed between the forward interior surface of the nose piece 470 and the point of attachment between the needle 415 and the spring 431. When the sharpened tip of the needle 415 is observed to emerge from the forward end of the catheter tube 499 to the desired contiguous position with the forward end of the catheter tube 499, further rearward movement of the catheter hub is stopped. The catheter hub 493 may then be held at that position for a sufficient time for the adhesive to set. Alternatively, the nose piece may be sized to be adequately frictionally held within the forward end of the barrel to resist dislodgement by the force exerted thereon by the compressed spring.

The actuating member 453, rear cap 465, and lever arm 427 are assembled as follows. The tabs 428 of the lever arm 427 are inserted into the slots 429 on the rear cap 465 to effectuate a snap fit between the lever arm 427 and the rear cap 465. The rear end 457 of the actuating member 453 is then inserted into the forward end 424 of the rear cap 465.

The forward end 455 of the actuating member 453 is then inserted into the rear end of the barrel 403. As the actuating member 453 is advanced within the barrel 403, the catching member 432 is positioned so that the shoulder 434 abuts with the surface 446 of the barrel 403. The catheter 490 can then be positioned over the needle 415 until the catheter hub 493 abuts the radial flange 486 of the nose piece 470. The front cap 479 is then positioned over the needle 415 and catheter 490.

Prior to use of the device, the front cap 479 is removed from the barrel 403. The needle 415 can then be inserted into a patient's blood vessel. As the needle 415 is inserted, the catheter tubing 499 also enters the blood vessel of the patient. The user verifies that the needle 415 is properly inserted in the patient's blood vessel by looking for the appearance of blood in the flashback chamber 451. After the needle 415 and catheter 490 have been properly inserted into the patient, the needle 415 is withdrawn from the patient's blood vessel while maintaining the forward end of the catheter tubing 499 within the patient's blood vessel.

The needle 415 can now be retracted by the user. To initiate retraction, the user presses the lever arm 427 toward the barrel 403, thereby moving the shoulder 434 of the catching member 432 out of abutment with the exposed surface 446 of the barrel 403. While continuing to depress the catching member 432 into the release position, the user applies pressure to the rear end 425 of the rear cap 465. Such simultaneous dual action allows the rear cap 465 and actuating member 453 to move in the forward direction. Movement of the actuating member 453 in the forward direction relative to the barrel 403 brings the tapered head 466 into contact with the fingers 447 of the needle retainer 441 to break the bond between the fingers and needle. Retraction of the needle is then accomplished in the same manner as described above in reference to the embodiment of FIG. 1.

As can be appreciated, needle retraction thus requires the user to simultaneously apply force to move two parts of the device in respective distinct directions. As can also be appreciated a variety of structural variations are possible to require such a dual action, other than the specific cantilever arm arrangement described herein. In other embodiments, means for preventing motion of the actuating member can be provided by any structure that restrains movement of the actuating member and requires the user to apply an operative force to a locking mechanism, in addition to the force applied to the actuating member.

Figure 14:
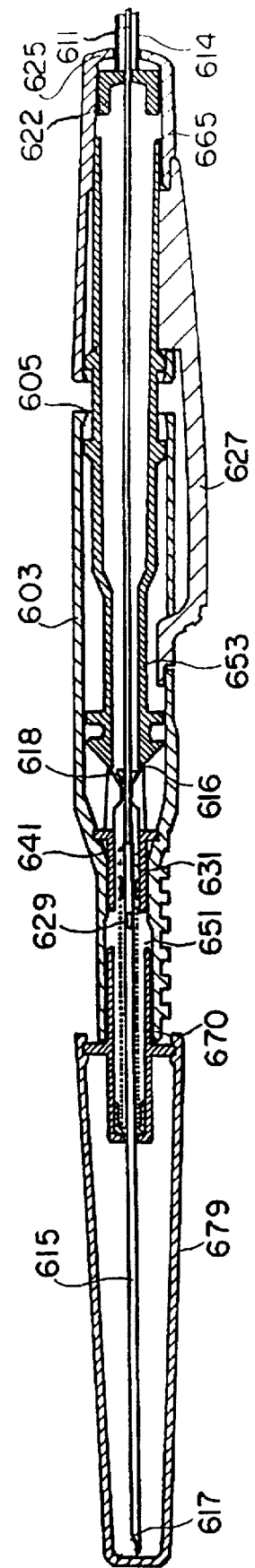
FIG. 14 is a sectional view of a guide wire insertion device in accordance with the present invention.

Referring to FIG. 14, there is shown a guide wire insertion device for a peripherally-inserted cardiac catheter (PICC) in accordance with the present invention. The device comprises a barrel 603 and an actuating assembly 651 inserted within the rear end 605 of the barrel 603. A needle retainer 641 and nosepiece 670 are provided to releasably maintain a needle 615 in a projecting configuration from the barrel 603. A guide wire 611 is also provided for insertion into a blood vessel of a patient. It should be noted that those elements of the guide wire insertion device which are similar to the elements of the embodiment of the catheter insertion device of FIG. 11 are designated by adding 200 to the reference numerals used for those elements with respect to the catheter insertion device.

The rear cap 665 of the guide wire insertion device includes a partially open rear end 625, which allows for the passage of the guide wire 611 therethrough. A membrane plug or seal 662 is provided within the interior of the cap 665. The membrane plug 662 is sufficiently resilient to provide a fluid-tight seal around the partially open rear end 625 of cap 665 both when the guide wire 611 is inserted within the insertion device and when the guide wire 611 is removed from the device. A protective tubing 614 can be provided concentrically around the guide wire 611 to protect the guide wire 611 as the insertion device is being used or operated. As shown, the protective tubing 614 surrounds the guide wire 611, projects through the partially open rear end 625 of the rear cap 665, and abuts the membrane seal 662.

The guide wire 611 passes through the partially open rear end 625 of the rear cap 665, through the membrane plug 662, and into the rear end 618 of the needle 615. Accordingly, the rear end 618 of the needle 615 does not have a plug, as was discussed in reference to the needle 415 of the catheter insertion device. Instead, the rear end 618 of the needle 615 is open to allow the guide wire 611 to be inserted within the interior of the needle 615. The guide wire 611 prevents blood from passing through the rear end 618 of the needle 615, when the needle 617 is inserted into the patient. The rear end 618 of the needle 615 comprises a flared portion 616 to facilitate insertion of the guide wire 611 into the needle 615 during assembly.

In assembly, the needle 615, spring 631, needle retainer 641, nose piece 670, and barrel 603 are assembled as described above in reference to the catheter insertion device. The actuating member 653, rear cap 665, and lever arm 627 are also assembled as described above. Once the actuating member 653, rear cap 665, and lever arm 627 are assembled, the membrane seal 662 is positioned within the rear cap 665. The actuating member 653, rear cap 665, and lever arm 627 are then attached to the barrel 603 as described above. Then, the protective cap 679 is positioned over the needle 615.

Prior to use, the protective tubing 614 is positioned within the partially open rear end 625 of the rear cap 665 to abut the membrane seal 662. The guide wire 611 is inserted within the protective tubing 614 and through the membrane seal 662. The forward end of the guide wire 611 is inserted within the rear end 618 of the needle 615, so that the forward end of the guide wire 611 is positioned within the needle, preferably to the rear of the hole 629. The protective cap 679 is now removed and the device is ready for use.

The tip 617 of needle 615 is inserted into the blood vessel of the patient. Correct placement of the needle 615 is verified by the appearance of blood in the flashback chamber 651. With the needle 615 in place, the protective tubing 614 is disconnected from the device and the forward end of the guide wire 611 is advanced through the needle 615 and into the patient's blood vessel. The device is then removed from the guide wire 611 by sliding the device rearwardly along the guide wire 611 while maintaining the guide wire 611 within the patient's vein. Once the device has been removed from the guide wire 611, the needle 615 can be retracted in the same manner as described above in reference to the catheter insertion device.

It should be appreciated that the structure disclosed herein for retaining the needle, as well as the structure for releasing the fingers of the needle retainer from the needle by breaking a bond therebetween, are applicable to a wide variety of medical devices other than the fluid collection device, the catheter insertion device, and the catheter and guide wire insertion devices described herein. For example, the needle holding and retraction arrangement can be used in syringes and pre-filled syringe ampoules to effect selective holding and retraction of the needles in such devices. The retraction of the needle enhances the safety of personnel engaged in the use and/or disposal of such devices, and further prevents reuse of used devices. Moreover, the confidence of the user is enhanced by the provision of a means for preventing premature retraction of the needle. In needle-bearing devices constructed in accordance with the foregoing principles, a compound action for needle retraction, requiring simultaneous operative forces to be applied to distinct portions of the device, is required.

The terms and expressions which have been employed are used as terms of description and not of limitation. There is no intention in the use of such terms and expressions of excluding any equivalents of the features shown and described or portions thereof. It will be recognized by those skilled in the art that changes or modifications may be made to the above-described embodiments without departing from the broad inventive concepts of the invention. It should therefore be understood that this invention is not limited to the particular embodiments shown and described herein, but is intended to include all changes and modifications that are within the scope and spirit of the invention as set forth in the claims.

That which is claimed is:

1. A catheter insertion device for positioning a catheter in a blood vessel of a patient, the catheter comprising a hub and a cannula connected with the hub, the device comprising:

a barrel having a forward end contoured to mate with an interior surface of the catheter hub;

a needle projecting forward from the barrel and having a sharpened tip extending beyond a forward end of the catheter cannula for penetrating the skin of the patient; and a needle retraction mechanism positioned in the barrel and operable by the user to effect retraction of the needle into the barrel after use;

the needle retraction mechanism comprising:
     a spring for exerting a rearward bias upon the needle;
     a needle retainer for releasably holding the needle in the projecting orientation against the bias of the spring;
     an actuating member positioned axially within the barrel and movable therein for releasing the needle retainer from holding the needle, the actuating member having a first actuation surface operable for effecting movement of the actuating member;
     stop means for preventing movement of the actuating member, the stop means having a second actuation surface operable to allow movement of the actuating member, whereby operation of the first and second actuating surfaces is required to effect retraction of the needle into the barrel.

2. The device of claim 1 wherein the stop means comprises a lever arm configured to prevent movement of the actuating member.

3. The device of claim 1 wherein the first and second actuating surfaces are configured to be operated along distinct directional axes.

4. The device of claim 3 wherein the actuating member comprises a tubular member positioned in the barrel and axially advanceable therein to release the needle retainer from holding the needle.

5. The catheter insertion device of claim 1 wherein said needle comprises a hollow shaft having said sharpened tip at the forward end thereof, a closed rear end, and is formed to have a lateral opening within the shaft at a location proximate the rear end.

6. The catheter insertion device of claim 5 wherein the needle retainer is positioned axially within the barrel to define a rear end of a flashback chamber in the forward end of the barrel, and configured to provide a fluid seal with the needle at a position along the needle to the rear of the lateral opening within the shaft of the needle.

7. The catheter insertion device of claim 6 wherein at least one of the needle retainer and the barrel is formed to provide selective vent means for selectively venting gas from the flashback chamber.

8. The catheter insertion device of claim 1 comprising catheter stabilizing means for interengaging with the hub of the catheter to prevent rotation thereof.

9. The catheter insertion device of claim 1 or 4, wherein the spring proximate one end thereof is bonded to the exterior of the needle for exerting the rearward bias and the needle retainer includes at least one axial surface bonded to the exterior of the exterior of the needle for holding the needle until released by the actuating member.

10. A medical device comprising a needle for puncturing the skin of a patient, comprising:

a barrel having a nose portion;

a spring connected with the needle for exerting a rearward bias on the needle;

a tubular needle retainer positioned in the barrel for releasably holding the needle in a projecting configuration from the forward end of the barrel, the needle retainer forming a fluid seal with the needle and forming a flashback chamber between the needle retainer and the nose portion of the barrel;

at least one of the barrel and the needle retainer having vent means formed therein for venting gas from the flashback chamber; and a hollow actuating member positioned in the barrel having an open forward end configured for releasing the needle retainer from the needle and for receiving the needle therein.

11. The medical device of claim 10, comprising actuation prevention means for preventing actuation of the actuating member and configured for simultaneous operation with the actuating member to permit actuation of the actuating member, whereby a compound motion is required to effect needle retraction.

12. The medical device of claim 11 comprising a catheter guide wire extending through the rear of the actuating member and having a forward end positioned within the needle.

13. The medical device of claim 10 comprising actuation prevention means for preventing actuation of the actuating member and configured for simultaneous operation with the actuating member to permit actuation of the actuating member, whereby a compound motion is required to effect needle retraction.

14. The medical device of claim 12 wherein the needle has a flared rear end for receiving the catheter guide wire.

15. The medical device of claim 10 wherein the needle is formed to have a lateral opening therein positioned along the needle in the flashback chamber when the needle is in the projecting configuration.

16. The medical device of claim 15 wherein the needle retainer comprises at least one axial surface bonded to the exterior of the needle for holding the needle until released by the actuating member, and wherein the needle has a closed rear end.

17. A method for assembling a catheter insertion device for guiding a catheter, which includes a hub and a cannula extending from the hub, the method comprising the steps of:

securing one end of a spring at a first attachment location to a needle having a sharp end;

securing the needle to a needle retainer at a second attachment location along the needle to the rear of the first attachment location;

positioning the needle retainer within a barrel having a bore in a forward end thereof so that the needle extends beyond the forward end of the bore;

positioning a nose piece, which is sized to be received within the bore, into the catheter hub;

urging the catheter hub axially rearwardly toward the front end of the barrel, so that the nose piece is received within the bore with the needle is received within the catheter cannula, and the spring is compressed against an interior forward surface of the nose piece;

fixing the nose piece to the bore of the housing when the sharpened end of the needle extends beyond the forward end of the catheter cannula by a predetermined distance.

* * * * *